United States Patent
Leflaive et al.

(10) Patent No.: US 7,718,842 B2
(45) Date of Patent: May 18, 2010

(54) PROCESS FOR SEPARATING META-XYLENE FROM A FEED OF AROMATIC HYDROCARBONS BY LIQUID PHASE ADSORPTION USING TETRALINE AS A DESORBANT

(75) Inventors: Philibert Leflaive, Mions (FR); Karin Barthelet, Lyons (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 525 days.

(21) Appl. No.: 11/501,230

(22) Filed: Aug. 9, 2006

(65) Prior Publication Data

US 2007/0043253 A1 Feb. 22, 2007

(30) Foreign Application Priority Data

Aug. 10, 2005 (FR) .................................. 05 52486

(51) Int. Cl.
*C07C 7/12* (2006.01)
(52) U.S. Cl. ..................... 585/828; 585/821; 585/822; 585/826; 585/827; 585/820
(58) Field of Classification Search ........................ None
See application file for complete search history.

(56) References Cited

U.S. PATENT DOCUMENTS

| 4,326,092 | A | | 4/1982 | Neuzil | |
|---|---|---|---|---|---|
| 4,886,930 | A | * | 12/1989 | Zinnen | 585/828 |
| 4,956,522 | A | * | 9/1990 | Zinnen | 585/828 |
| 5,057,643 | A | * | 10/1991 | Zinnen | 585/828 |
| 5,107,062 | A | * | 4/1992 | Zinnen | 585/828 |
| 5,171,922 | A | * | 12/1992 | Anderson | 585/805 |
| 5,177,295 | A | * | 1/1993 | Oroskar et al. | 585/805 |
| 5,382,747 | A | | 1/1995 | Kulprathipanja | |
| 5,495,061 | A | * | 2/1996 | Kulprathipanja | 585/828 |
| 5,849,981 | A | * | 12/1998 | Kulprathipanja | 585/828 |
| 5,900,523 | A | | 5/1999 | Kulprathipanja | |
| 6,410,815 | B1 | | 6/2002 | Plee | |

* cited by examiner

*Primary Examiner*—Tam M Nguyen
(74) *Attorney, Agent, or Firm*—Millen, White, Zelano & Branigan, P.C.

(57) ABSTRACT

The invention concerns a process for separating meta-xylene from a hydrocarbon feed comprising isomers containing 8 carbon atoms, comprising:
  a step for bringing said feed into contact with a faujasite type zeolite adsorbant, the percentage of water in the adsorbant being in the range 0 to 8% by weight and the adsorption temperature being from 25° C. to 250° C.;
  a desorption step employing a solvent selected from tetraline and its alkylated derivatives;
  a step for separating meta-xylene from the desorbant.

18 Claims, 1 Drawing Sheet

PROCESS FOR SEPARATING META-XYLENE FROM A FEED OF AROMATIC HYDROCARBONS BY LIQUID PHASE ADSORPTION USING TETRALINE AS A DESORBANT

FIELD OF THE INVENTION

The present invention relates to a process for separating meta-xylene from a feed of aromatic hydrocarbons comprising isomers containing 8 carbon atoms, by liquid phase adsorption.

In particular, this process is of application to the preparation of very pure meta-xylene, i.e. a meta-xylene having a purity of more than 99.0%, preferably more than 99.5%.

The meta-xylene from said process can be used for the preparation of insecticides or chemical intermediates such as isophthalic acid.

PRIOR ART

Initially, meta-xylene was separated from aromatic feeds by conventional separation techniques which include chemical extraction by suitable chemical agents or extractive distillation.

U.S. Pat. No. 4,585,526 describes the separation of meta-xylene from aromatic hydrocarbon feeds primarily comprising ortho-xylene by bringing said feed into contact with extracting agents such as propoxypropanol, 1,4-butanediol, ethyl benzoate, ethylene glycol phenylether or benzyl alcohol. However, that technique cannot produce the very pure meta-xylene defined above, because the extracting agents are not sufficiently selective.

U.S. Pat. No. 3,700,744, U.S. Pat. No. 3,729,523 and U.S. Pat. No. 3,773,846 describe the separation of meta-xylene from aromatic feeds, using an extractive distillation step. However, the molecules present in the sample to be distilled often have boiling points which are close together, rendering separation by distillation difficult and expensive.

To overcome those disadvantages, some authors proposed separating the meta-xylene from aromatic hydrocarbon feeds by bringing the feeds into the presence of a zeolite type selective adsorbant. Thus, U.S. Pat. No. 4,306,107 describes the use, as a selective adsorbant for meta-xylene, of a Y zeolite in which the exchangeable cationic sites are occupied by sodium atoms. To obtain a satisfactory selectivity in favour of meta-xylene, it is recommended that partially hydrated zeolite be used, with a loss on ignition at 500° C. of 2% to 7% by weight of the initial zeolite weight. That document recommends separation by a simulated moving bed process at a temperature in the range 20° C. to 250° C. and at a pressure in the range from atmospheric pressure to 35 bars, the value being selected to maintain the feed in the liquid form. The desorbant which is selected is toluene.

U.S. Pat. No. 5,382,747 describes the use of a Y zeolite in which the cationic sites are simultaneously occupied by sodium and lithium cations (5 molar % to 35 molar % exchange of sodium cations, preferably 10 molar % to 30 molar %), said zeolite having a loss on ignition at 500° C. in the range 1.5% to 3% by weight. The adsorption temperature is between 100° C. and 145° C. and the desorbant used is toluene or indane.

U.S. Pat. No. 5,900,523 describes the use of a Y zeolite with a silica/alumina ratio in the range 4 to 6, in which the cationic sites are occupied by sodium cations, having:

a loss on ignition at 500° C. in the range 1.5% to 2% by weight and an adsorption temperature in the range 100° C. to 150° C., when the desorbant is toluene;

a loss on ignition at 500° C. in the range 1.5% to 2.5% by weight and an adsorption temperature in the range 100° C. to 150° C. when the desorbant is indane.

The adsorption based processes described in the documents mentioned above all allow the separation of meta-xylene with good selectivity for meta-xylene compared with the other constituents of the feed.

The inventors aimed to provide a process for separating meta-xylene from an aromatic hydrocarbon feed which can separate meta-xylene with a selectivity which is substantially identical or even better than that obtained with prior art processes, an adsorbant capacity which is substantially identical to or better than that obtained with the prior art processes, and moreover, which can separate meta-xylene with an improved matter transfer. The term "matter transfer" means the rate of diffusion of the compounds of the feed (in this case, preferably meta-xylene) in the adsorbant.

DISCLOSURE OF THE INVENTION

The invention provides a process for separating meta-xylene from a hydrocarbon feed comprising isomers containing 8 carbon atoms, comprising:

a step for bringing said feed into contact with a metaselective adsorbant comprising a faujasite type zeolite, the percentage of water in said zeolite being in the range 0 to 8% by weight and the adsorption temperature being from 25° C. to 250° C.;

a desorption step employing a desorbant selected from tetraline and its alkylated derivatives;

a step for separating meta-xylene from said desorbant.

The expression "hydrocarbon feed comprising isomers containing 8 carbon atoms" generally means a feed comprising isomers of meta-xylene such as ortho-xylene, para-xylene or ethylbenzene.

Further, the use of tetraline as a desorbant has the advantage of allowing ready separation of the meta-xylene from the desorbant during the final separation step, for example by distillation, because of the large boiling point difference between tetraline and meta-xylene (respectively 207° C. for tetraline and 139° C. for meta-xylene at atmospheric pressure). As a result, the tetraline can readily be recovered for re-use during a subsequent desorption cycle.

The cost of separating tetraline from meta-xylene is thus lower compared with the prior art which uses desorbants having boiling points close to that of meta-xylene.

As mentioned above, the adsorbant is a metaselective faujasite zeolite type adsorbant.

The term "metaselective adsorbant" as used in the context of the invention means an adsorbant which allows preferential adsorption of meta-xylene compared with the other constituents of the feed, in particular compared with the $C_8$ aromatic compounds of the feed, such as para-xylene, ortho-xylene or ethylbenzene.

Two categories of faujasites may be envisaged in the context of the invention:

X faujasites for which the (Si/Al) ratio is 1.0 to 1.5;

Y faujasites for which the (Si/Al) ratio is more than 1.5 which can, for example, be up to 6, preferably 2.5 to 3.0.

In general, the Y faujasites used in the context of the present invention have the following general formula:

$(1\pm 0.1)M_{2/n}O{:}Al_2O_3{:}wSiO_2{:}yH_2O$ in which:

M represents an alkali or alkaline-earth metal;

w, represents the number of moles of $SiO_2$;

y, representing the number of moles of $H_2O$, is 8 or less;

n represents the valency of the alkali or alkaline-earth metal.

When w is less than 3, the faujasites correspond to X faujasites, as defined above.

When w is more than 3, the faujasites correspond to Y faujasites, as defined above.

Preferably, in accordance with the invention, the faujasites are Y faujasites essentially containing only sodium, i.e. a faujasite wherein at least 70% of the sites, preferably at least 90%, are occupied by sodium ions, any other exchangeable sites being occupied by alkali or alkaline-earth ions other than sodium.

Preferably, the (Si/Al) ratio of said faujasite is in the range 2.5 to 3.0.

Examples of suitable sodium-containing zeolites of the invention are given in U.S. Pat. No. 4,326,092; U.S. Pat. No. 5,382,747; and U.S. Pat. No. 5,900,523.

Generally, the adsorbant of the invention is in the form of an agglomerate comprising crystals of faujasite type zeolite, preferably Y zeolite, dispersed in an inorganic binder, such as alumina or clay, the amount of inorganic binder generally not exceeding 25% by weight of the total weight of the adsorbant.

The quantity of Y faujasite present in the agglomerate is generally in the range 75% to 98% by weight with respect to the total weight of the agglomerate.

The agglomerate is generally prepared from faujasite powders using methods known to the skilled person, to form hard particles such as extrudates, aggregates or beads of a defined size range.

The particles mentioned above may have an average size of 100 micrometers to a few millimetres.

In accordance with the invention, the zeolites used have a water content of 0 to 8% by weight with respect to the total weight of the zeolite, preferably 0 to 1% by weight.

When the zeolite has a water content of 0 to 1% by weight, to achieve such a water content, prior to contact with the hydrocarbon feed, the zeolite advantageously undergoes a specific pre-treatment step which can reduce the amount of moisture in the zeolite and also activate it so that it can achieve better matter transfer and adsorb a larger quantity of meta-xylene.

Said pre-treatment step comprises:

at least one drying stage at a constant temperature of 60° C. to 120° C. for a period of 0.5 hours to 3 hours; and at least one activation stage at a constant temperature of at least 235° C., the temperature being up to 500° C., for a period of 0.5 hours to 3 hours.

Preferably, said pre-treatment step is carried out in an inert gas atmosphere, such as nitrogen, or in a dry air atmosphere to minimize the presence of moisture in the atmosphere.

It is preferable to opt for a steady rise in temperature between the constant temperature drying and activation stages, said rise being at a rate of 1° to 50° C./min, for example.

Other intermediate constant temperature stages between the drying stage and the activation stage may be provided.

Between the intermediate stages, it is also recommended that the temperature rise should be slow, as defined above.

Thus, for example, when the zeolite is to be activated at 400° C., after a constant temperature drying stage at 80° C., stages at 150° C., 200° C., 250° C. and 300° C. may be instigated. As an example, the drying stage at 80° C. and the activation stage at 400° C. may be maintained for 0.1 hour, while the intermediate stages may be maintained for 45 minutes.

Between the various constant temperature stages, the temperature may, for example, be increased linearly at a rate of 5° C./min.

This pre-treatment step may be carried out using a plurality of furnaces disposed in series, each furnace being dedicated to employing a constant temperature stage, or using a single programmed furnace to implement the various constant temperature stages.

Parameters such as the gas supply rate and the adsorbant supply rate may readily be adjusted by the skilled person.

This pre-treatment step can prevent even slight degradation of the properties of the adsorbant during the process.

At the end of said pre-treatment step, a partially or completely dehydrated adsorbant is obtained with a water content of 0 to 1% by weight with respect to the total weight of zeolite.

Because of the degree of hydration obtained at the end of this step, the zeolites are stable at very high temperatures (for example of the order of 700° C. to 800° C.) without risking a loss of crystallinity, or degradation by a dealumination reaction.

The amount of water defined above is determined by measuring the loss on ignition at 500° C. (LOI), defined as the percentage weight loss underwent by the adsorbant at an effective temperature of 500° C. in a purge of dry inert gas, such as nitrogen, for a sufficiently long period (generally one to two hours) so that its weight remains constant after said period. This loss on ignition is expressed with respect to the initial mass of the adsorbant.

In the case of a new adsorbant (i.e. an adsorbant prior to its first use) of the faujasite type as mentioned above, the loss on ignition corresponds almost exclusively to a loss of water. The loss can thus generally be considered as a measure of the water content of the adsorbant. The actual quantity of water on adsorbants can, however, be determined by analytical methods such as the Karl Fischer method (ASTM D1364).

According to the invention, the hydrocarbon feed is brought into contact with the adsorbant, preferably pretreated, and at an adsorption temperature of 25° C. to 250° C., preferably 100° C. to 200° C., and more preferably 120° C. to 180° C. The operating pressure may be in the range from atmospheric pressure to 20 bars.

The operating conditions employed in the context of the contact step renders possible highly selective adsorption of meta-xylene on the adsorbant as well as excellent matter transfer.

In the foregoing, the term "selectivity of adsorbant for meta-xylene compared with other compounds of a mixture (defined by the abbreviation X) which is brought into contact with the adsorbant" means the ratio of concentrations as defined below:

$$[(metaxyl)_z/(X)_z]/[(metaxyl)_s/(X)_s]$$

in which:

$(metaxyl)_z$ and $(metaxyl)_s$ represent the concentrations by weight of meta-xylene respectively in the adsorbant and in the mixture at equilibrium after passage over the adsorbant;

$(X)_z$ and $(X)_s$ represent the concentrations by weight of other compounds respectively in the adsorbant and in the mixture at equilibrium after passage over the adsorbant.

Equilibrium is reached when the composition of the mixture traversing the bed of adsorbant no longer changes, in other words when there is no more net transfer of matter occurring between the adsorbed phases and non adsorbed phases.

When the selectivity as defined above is close to 1, this means that the meta-xylene and the other compounds are adsorbed in almost identical quantities. In other words, this means that there is no preferential adsorption when comparing compounds.

When the selectivity is over 1, this means that meta-xylene is preferentially adsorbed over the other compounds of the mixture.

Preferably, the selectivity of meta-xylene compared with the other constituents of the feed should be more than 1.5.

A technique of choice for determining the selectivity of the adsorbant for meta-xylene may consist of producing breakthrough curves as explained in the work by Ruthven, "Principles of Adsorption and Adsorption Processes" (pages 220-273).

To estimate the matter transfer between the adsorbant and the feed, it is possible to use plate theory, as explained in Ruthven's work "Principles of Adsorption and Adsorption Processes" (Chapter 8, pages 248-250)

The process of the invention comprises a desorption step consisting of passing a stream of tetraline or a stream of one of its alkylated derivatives over the adsorbant.

Alkylated tetraline derivatives which may be cited are methyl tetraline, ethyl tetraline, propyl tetraline, isopropyl tetraline, methylethyl tetraline, dimethyl tetraline and diethyl tetraline. Clearly, the term "alkylated tetraline derivatives" encompasses all positional isomers.

The tetraline (or its alkylated derivatives) used as a desorbant has the following advantages:

good compatibility with the feed and the adsorbant, in that they cause neither reduction nor inversion of selectivity for meta-xylene with respect to the other compounds present in the feed;

non-reactivity as regards meta-xylene and/or adsorbant;

sufficient force to fairly quickly displace the meta-xylene without consuming too much tetraline;

good diffusivity in the adsorbant;

a boiling point which differs substantially from meta-xylene, thereby allowing easy separation of tetraline and meta-xylene by simple distillation.

The desorption step is advantageously carried out at a temperature and pressure similar to those used in the context of the adsorption step described above.

Preferably, the volume ratio of the desorbant to the feed is from 0.5 to 2.5, preferably 1 to 2.

After the first two steps (adsorption step and desorption step), a first stream comprising the desorbant is obtained from the reactor outlet along with the compounds which are the least selectively adsorbed (said first stream corresponds to the first passage(s) of the desorbant over the adsorbant) and a second stream comprising desorbant and meta-xylene (said second stream corresponding to the subsequent passage(s) of the desorbant over the adsorbant).

The first stream may, for example, be separated by distillation into two streams:

a stream comprising the desorbant;

a stream comprising the compounds of the feed which are the least selectively adsorbed.

In accordance with the invention, the second stream is treated, for example by distillation, to separate the meta-xylene from the desorbant.

The recovered tetraline may then be re-used in a subsequent step.

Any equipment which allows the bed of solid adsorbant to come into contact with the feed to be treated may be used to carry out the process of the invention.

Thus, according to one implementation of the invention (batch mode), the adsorbant is in the form of one or more fixed beds which are alternately brought into contact with the feed and the desorbant.

According to another implementation (continuous mode), the contact with the adsorbant may be made using a technique known as the simulated moving bed technique, preferably in counter-current mode. That technique is carried out in the direction of flow of a principal stream moving in said column, periodically simultaneously displacing the positions for injecting the feed to be treated and the desorbant and the positions for withdrawing the extract (meta-xylene+desorbant) and raffinate (other compounds of the feed+desorbant). A unit comprising 12 to 24 beds may be used in this technique.

The invention will now be described with respect to the following examples, given by way of non limiting example.

DETAILED DESCRIPTION OF PARTICULAR IMPLEMENTATIONS

Example 1

In this example, a breakthrough test (frontal chromatography) was carried out to determine the efficacy of toluene in separating meta-xylene from a meta-xylene/ortho-xylene mixture using the operating conditions described in U.S. Pat. No. 4,306,107, i.e. with an adsorbant having a loss on ignition (determined at 500° C.) of 2.3% and an adsorption temperature of 120° C. then using the operating conditions described in U.S. Pat. No. 5,900,523, i.e. with an adsorbant having a loss on ignition (determined at 500° C.) of 1.75% by weight, and an adsorption temperature of 125° C.

The composition of the feed was as follows:

meta-xylene: 45% by weight;

ortho-xylene: 45% by weight isooctane: 10% by weight (isooctane being used as a tracer to estimate the non selective volumes and is not involved in the separation).

The adsorbant was a Y type faujasite substituted with sodium. The quantity of adsorbant used for these tests was about 55 g.

The activations necessary for achieving losses on ignition of 1.75% and 2.3% by weight respectively were carried out ex situ in a tube furnace using a nitrogen flow of 40 l/h.

The operating procedure used to obtain the breakthrough and breakout curves was as follows:
1) filling the column with adsorbant and placing the column on the test bench;
2) filling with toluene at ambient temperature;
3) steadily increasing the adsorption temperature in a stream of toluene (5 cm³/min);
4) injecting toluene at 10 cm³/min when the adsorption temperature is reached;
5) withdrawing toluene to allow feed injection;
6) injecting the feed (10 cm³/min), injection being maintained for a period sufficient to reach thermodynamic equilibrium;
7) collecting and analyzing the breakthrough effluent;
8) withdrawing the feed to inject the desorption solvent (toluene);
9) injecting the desorption solvent (toluene) (10 cm³/min) for a period sufficient to desorb compounds adsorbed on the adsorbant;
10) collecting and analyzing the breakthrough effluent.

The pressure for said tests was maintained at 10 bars so that the feed and solvents mentioned above remained in the liquid phase.

The results of the two breakthroughs are shown in Table 1 below.

The selectivity for meta-xylene compared with ortho-xylene was calculated using the material balance. The selectivity of the meta-xylene over tetraline was calculated by simulating the experimental curve (breakthrough and breakout).

The results of the various breakthroughs are shown in Table 1 below.

constant temperature stages to 80° C., 150° C., 200° C., 250° C., 300° C. and 400° C. Between the constant temperature stages, the temperature was increased linearly at a rate of 5° C./min.

Figure 1:
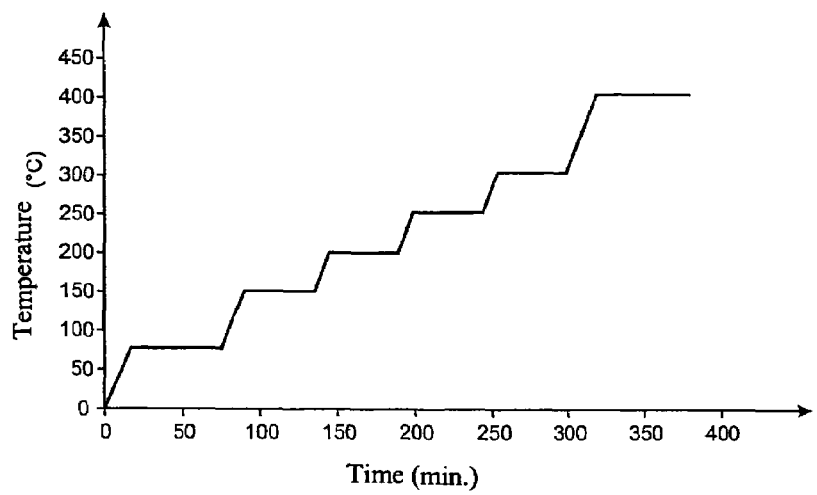
FIG. 1 represents the temperature profile followed to pretreat an adsorbant used in Example 2.

The temperature was kept at 80° C. and 400° C. for 1 hour, and for 45 minutes at the other stages. The temperature profile followed to activate the adsorbant is given in FIG. 1.

The mass of adsorbant after activation was 55.3 g.

The residual loss on ignition at 500° C. was less than 0.05%.

The operating procedure used to obtain the breakthrough curves was as follows:
1) filling the column with adsorbant and placing the column on the test bench;
2) filling with tetraline at ambient temperature;
3) steadily increasing the adsorption temperature (160° C.) in a stream of tetraline (5 cm³/min);
4) injecting tetraline at 10 cm³/min when the adsorption temperature (160° C.) is reached;
5) withdrawing tetraline to allow feed injection;
6) injecting the feed (10 cm³/min), injection being maintained for a period sufficient to reach thermodynamic equilibrium;
7) collecting and analyzing the breakthrough effluent;
8) withdrawing the feed to inject the desorption solvent (tetraline);
9) injecting the desorption solvent (tetraline) (10 cm³/min) for a period sufficient to desorb compounds adsorbed on the adsorbant;
10) collecting and analyzing the breakthrough effluent.

During the test, the column temperature was maintained at 160° C. and the pressure was maintained at 10 bars so that the feed and solvents mentioned above remained in the liquid phase.

The composition of the feed was as follows:
meta-xylene: 45% by weight;
ortho-xylene: 45% by weight

TABLE 1

| Nature of adsorbant | LOI[1] at 500° C. | Temperature[2] | Capacity* | Selectivity[3] $\alpha_{MX/OX}$ | Selectivity[4] $\alpha_{MX/solv}$ | Theoretical plate height |
|---|---|---|---|---|---|---|
| NaY | 2.3% | 120° C. | 0.185 | 1.78 | 1.11 | 3.94 |
| NaY | 1.75% | 125° C. | 0.186 | 1.92 | 1.25 | 4.79 |

[1]LOI: loss on ignition
[2]Temperature: adsorption temperature
[3]$\alpha_{MX/OX}$: selectivity of meta-xylene compared with ortho-xylene
[4]$\alpha_{MX/solv}$: selectivity of meta-xylene compared with the desorption solvent
*The capacity is expressed in grams of $C_8$ aromatic compounds adsorbed per gram of adsorbant Example 2

In this example, a breakthrough test (frontal chromatography) was carried out to determine the efficacy of tetraline in separating meta-xylene from a meta-xylene/ortho-xylene mixture.

The adsorbant used was a Y faujasite type zeolite substituted with sodium (denoted NaY) with a loss on ignition at 500° C. of less than 0.05% by weight. The adsorption temperature (like the desorption temperature) was fixed at 160° C.

The quantity of adsorbant used for the test before activation was 56.6 g.

The adsorbant was then pre-treated to activate it in situ by injecting nitrogen into the column at a flow rate of 40 l/h at ambient temperature, then the temperature was increased in isooctane: 10% by weight (this being used as a tracer to estimate the non selective volumes and not involved in the separation).

The desorbant used was tetraline or 1,2,3,4-tetrahydronaphthalene.

During breakthrough and breakout, the effluent from the column was sampled (80 samples) then analyzed by gas chromatography to determine its composition at various time intervals.

Figure 2:
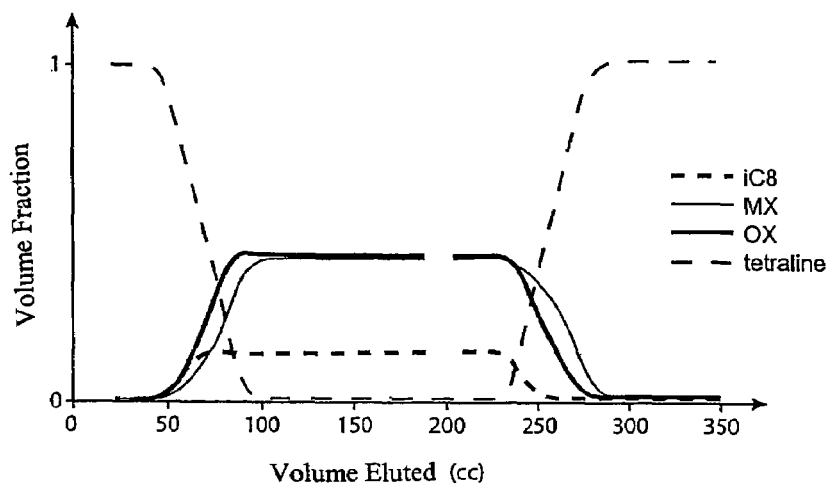
FIG. 2 shows a chromatographic representation of the separation of meta-xylene from a meta-xylene/ortho-xylene mixture at 160° C., over a Y faujasite type adsorbant, with a loss on ignition at 500° C. of less than 0.05% by weight and with tetraline as the desorbant.

The breakthrough and breakout curves corresponding to that feed and to the desorption solvent are given in FIG. 2.

The capacity of the adsorbant and its selectivity were calculated and are given in Table 2 below. The selectivity of meta-xylene with respect to ortho-xylene was calculated using the material balance.

The selectivity of meta-xylene compared with tetraline was calculated by simulating the experimental curve (breakthrough and breakout).

TABLE 2

| Nature of adsorbant | Capacity* | Selectivity[3] $\alpha_{MX/OX}$ | Selectivity[4] $\alpha_{MX/solv}$ | Theoretical plate height |
|---|---|---|---|---|
| NaY | 0.185 | 1.84 | 1.05 | 3.08 |

[3]$\alpha_{MX/OX}$: selectivity of meta-xylene compared with ortho-xylene
[4]$\alpha_{MX/solv}$: selectivity of meta-xylene compared with the desorption solvent
*The capacity is expressed in grams of $C_8$ aromatic compounds adsorbed per gram of adsorbant The results obtained indicate that the meta-xylene/solvent selectivity is particularly good. Similarly, the diffusion of meta-xylene in the adsorbant is particularly satisfactory because the theoretical plate height is rather low, as calculated from the breakthrough data.

Example 3

In this example, a breakthrough test (frontal chromatography) was carried out to determine the efficacy of tetraline in separating meta-xylene from a meta-xylene/ortho-xylene mixture.

The adsorbant used was a Y faujasite type zeolite substituted with sodium (denoted NaY) with a loss on ignition of 500° C. of 2.2% by weight. The adsorption temperature (like the desorption temperature) was fixed at 140° C.

The quantity of adsorbant used for the test before activation was 55.9 g.

The activation necessary to achieve a loss on ignition at 500° C. of 2.2% by weight was carried out ex situ in a tube furnace using a nitrogen flow rate of 400 l/h.

The loss on ignition at 500° C. was less than 0.05%.

The operating procedure used to obtain the breakthrough and breakout curves comprised the following operations:
1) filling the column with adsorbant and placing the column on the test bench;
2) filling with tetraline at ambient temperature;
3) steadily increasing the adsorption temperature (140° C.) in a stream of tetraline (5 cm³/min);
4) injecting tetraline at 10 cm³/min when the adsorption temperature (140° C.) is reached;
5) withdrawing tetraline to allow feed injection;
6) injecting the feed (10 cm³/min), injection being maintained for a period sufficient to reach thermodynamic equilibrium;
7) collecting and analyzing the breakthrough effluent;
8) withdrawing the feed to inject the desorption solvent (tetraline);
9) injecting the desorption solvent (tetraline) (10 cm³/min) for a period sufficient to desorb compounds adsorbed on the adsorbant;
10) collecting and analyzing the breakthrough effluent.

During the test, the column temperature was maintained at 140° C. and the pressure was maintained at 10 bars so that the feed and solvents mentioned above remained in the liquid phase.

The composition of the feed was as follows:
meta-xylene: 45% by weight;
ortho-xylene: 45% by weight
isooctane: 10% by weight (this being used as a tracer to estimate the non selective volumes and not involved in the separation).

The desorbant used was tetraline or 1,2,3,4-tetrahydronaphthalene.

During the breakthrough and breakout, the effluent from the column was sampled (80 samples) then analyzed by gas chromatography to determine its composition at various time intervals.

Figure 3:
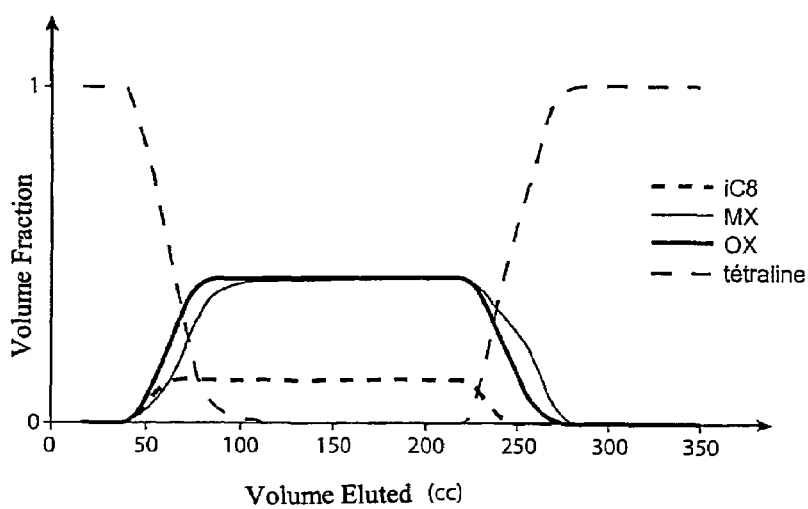
FIG. 3 shows a chromatographic representation of the separation of meta-xylene from a meta-xylene/ortho-xylene mixture at 140° C. over a Y faujasite type adsorbant, the loss on ignition at 500° C. of which is less than 2.2% by weight and with tetraline as the desorbant.

The breakthrough and breakout curves corresponding to that feed and to the desorption solvent are given in FIG. 3.

The capacity of the adsorbant and its selectivity were calculated and are given in Table 3 below. The selectivity of meta-xylene with respect to ortho-xylene was calculated using the material balance.

The selectivity of meta-xylene compared with tetraline was calculated by simulating the experimental curve (breakthrough and breakout).

TABLE 3

| Nature of adsorbant | Capacity* | Selectivity[3] $\alpha_{MX/OX}$ | Selectivity[4] $\alpha_{MX/solv}$ | Theoretical plate height |
|---|---|---|---|---|
| NaY | 0.190 | 1.92 | 1.09 | 3.76 |

[3]$\alpha_{MX/OX}$: selectivity of meta-xylene compared with ortho-xylene
[4]$\alpha_{MX/solv}$: selectivity of meta-xylene compared with the desorption solvent
*The capacity is expressed in grams of $C_8$ aromatic compounds adsorbed per gram of adsorbant The results obtained indicate that the meta-xylene/solvent selectivity is particularly good. Similarly, the diffusion of meta-xylene in the adsorbant is particularly satisfactory because the theoretical plate height is rather low, as calculated from the breakthrough data.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 05/52.486, filed Aug. 10, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for separating meta-xylene from a hydrocarbon feed comprising isomers containing 8 carbon atoms, comprising:
   a step for bringing said feed into contact with a metaselective adsorbant comprising a faujasite type zeolite, the percentage of water in said zeolite being in the range 0 to 8% by weight and the adsorption temperature being from 25° C. to 250° C.;
   a desorption step employing a desorbant; and
   a step for separating meta-xylene from said desorbant;
said process being characterized in that said desorbant is selected from the group consisting of tetraline methyl tetraline, ethyl tetraline, propyl tetraline, isopropyl tetraline, methylethyl tetraline, dimethyl tetraline and diethyl tetraline.

2. A meta-xylene separation process according to claim 1, in which the faujasite type zeolite is selected from:
X faujasites in which the (Si/Al) ratio is from 1.0 to 1.5;
Y faujasites in which the (Si/Al) ratio is more than 1.5.

3. A meta-xylene separation process according to claim 1, in which the faujasite type zeolite is a Y faujasite.

4. A meta-xylene separation process according to claim 3, in which the Y faujasite has exchangeable sites which are at least 70% occupied by sodium atoms.

5. A meta-xylene separation process according to claim 3, in which the faujasite has a (Si/Al) ratio of 2.5 to 3.

6. A meta-xylene separation process according to claim 1, in which the adsorbant is in the form of an agglomerate comprising faujasite type zeolite crystals dispersed in an inorganic binder.

7. A meta-xylene separation process according to claim 6, in which the faujasite is included in the agglomerate in an amount of 75% to 98% by weight with respect to the total agglomerate weight.

8. A meta-xylene separation process according to claim 1, in which the adsorbant has a water content of 0 to 1% by weight.

9. A meta-xylene separation process according to claim 8 comprising, prior to the contact step, an adsorbant pre-treatment step comprising:
at least one drying stage at a constant temperature of 60° C. to 120° C. for a period of 0.5 hours to 3 hours; and
at least one activation stage at a constant temperature of at least 235° C. for a period of 0.5 hours to 3 hours.

10. A meta-xylene separation process according to claim 9 in which, between the drying stage and the activation stage, the observed temperature rise is from 1 to 50° C./min.

11. A meta-xylene separation process according to claim 1, in which the adsorption temperature is from 100° C. to 200° C.

12. A meta-xylene separation process according to claim 11, in which the adsorption temperature is from 120° C. to 180° C.

13. A meta-xylene separation process according to claim 1, in which the desorbant has a volume ratio with respect to the feed of 0.5 to 2.5 by volume.

14. A meta-xylene separation process according to claim 13, in which the desorbant has a volume ratio with respect to the feed of 1 to 2 by volume.

15. A meta-xylene separation process according to claim 1, in which the operating pressure is from atmospheric pressure to 20 bars.

16. A meta-xylene separation process according to claim 1, in which the adsorbant is in the form of one or more fixed beds.

17. A meta-xylene separation process according to claim 1, in which contact with the adsorbant is carried out using a simulated moving bed technique.

18. A meta-xylene separation process according to claim 1, wherein the desorbant is tetraline.

* * * * *